United States Patent
Kishita et al.

(10) Patent No.: US 8,276,470 B2
(45) Date of Patent: *Oct. 2, 2012

(54) DEVICE AND METHOD FOR INTRODUCING GAS FOR ANALYSIS DEVICE

(75) Inventors: Keisuke Kishita, Toyota (JP); Hisashi Sakai, Seto (JP)

(73) Assignee: Toyota Jidosha Kabushiki Kaisha, Toyota-shi, Aichi-ken (JP)

(*) Notice: Subject to any disclaimer, the term of this patent is extended or adjusted under 35 U.S.C. 154(b) by 270 days.

This patent is subject to a terminal disclaimer.

(21) Appl. No.: 12/667,703

(22) PCT Filed: Jul. 10, 2008

(86) PCT No.: PCT/JP2008/062874
§ 371 (c)(1),
(2), (4) Date: Jan. 5, 2010

(87) PCT Pub. No.: WO2009/008549
PCT Pub. Date: Jan. 15, 2009

(65) Prior Publication Data
US 2011/0000323 A1    Jan. 6, 2011

(30) Foreign Application Priority Data
Jul. 12, 2007 (JP) .................. 2007-183292

(51) Int. Cl.
*G01N 1/00* (2006.01)
(52) U.S. Cl. .................................................. 73/864.81
(58) Field of Classification Search .............. 73/864.81, 73/863, 864.83, 23.2, 863.02
See application file for complete search history.

(56) References Cited

U.S. PATENT DOCUMENTS

| | | | |
|---|---|---|---|
| 6,865,926 B2 | 3/2005 | O'Brien et al. | 73/23.27 |
| 7,201,179 B2 | 4/2007 | Barr et al. | 137/3 |
| 2004/0031564 A1 | 2/2004 | Gottscho et al. | |
| 2005/0277246 A1 | 12/2005 | Kirkpatrick et al. | |

(Continued)

FOREIGN PATENT DOCUMENTS

EP    2 166 345    3/2010

(Continued)

OTHER PUBLICATIONS

Zhao, A. et al., "Small-volume, ultrahigh-vacuum-compatible high-pressure reaction cell for combined kinetic and in situ IR spectroscopic measurements on planar model catalysts," Review of Scientific Instruments, vol. 76, No. 12, (2005), pp. 123903-1-123903-8.

(Continued)

*Primary Examiner* — Peter Macchiarolo
*Assistant Examiner* — Tamiko Bellamy
(74) *Attorney, Agent, or Firm* — Finnegan, Henderson, Farabow, Garrett & Dunner, LLP

(57) ABSTRACT

Gas is supplied from positive pressure ($10^5$ Pa or more) to an analysis device of high vacuum ($10^{-2}$ Pa or less) precisely and stably, while keeping conditions constant and replicating the conditions, and performing switching to a desired gas within a short time. According to a gas introducing device and a method, a plurality of types of gases are synthesized in a mixing chamber, the synthesized gas is introduced and the pressure of the gas is reduced by a pressure reducing pump to a pressure ranging from 0.1 Pa to 0.1 MPa, and the depressurized gas is introduced to a gas analysis device through a switching operation using a gas switching valve.

6 Claims, 2 Drawing Sheets

U.S. PATENT DOCUMENTS

| | | |
|---|---|---|
| 2006/0144126 A1 | 7/2006 | O'Brien et al. .............. 73/23.42 |
| 2007/0160325 A1 | 7/2007 | Son et al. ......................... 385/37 |
| 2007/0194251 A1 | 8/2007 | Ward et al. ............... 250/492.21 |
| 2010/0005854 A1* | 1/2010 | Koster et al. ..................... 73/23.2 |
| 2010/0077873 A1 | 4/2010 | Kishita et al. .............. 73/863.01 |

FOREIGN PATENT DOCUMENTS

| | | |
|---|---|---|
| JP | 4-10349 | 1/1992 |
| JP | 4-32144 | 2/1992 |
| JP | 05134099 | 5/1993 |
| JP | 05188019 | 7/1993 |
| JP | 05196583 | 8/1993 |
| JP | 5-64729 | 9/1993 |
| JP | 5-332958 | 12/1993 |
| JP | 8-68732 | 3/1996 |
| JP | 2571071 | 10/1996 |
| JP | 10-104141 | 4/1998 |
| JP | 10-274644 | 10/1998 |
| JP | 2912105 | 4/1999 |
| JP | 11-183462 | 7/1999 |
| JP | 2001-50868 | 2/2001 |
| JP | 2003-340270 | 12/2003 |
| JP | 3888577 | 12/2006 |
| JP | 2007-101298 | 4/2007 |

OTHER PUBLICATIONS

Frattolillo, A. et al., "Quantitative detection of tiny amounts of helium isotopes in a hydrogen isotope atmosphere using a standard-resolution quadrupole mass spectrometer," J. Vac. Sci. Technol. A, vol. 25, No. 1, (2007), pp. 75-89.

Extended European Search Report for EP Appl. No. 08778225.6 dated Feb. 22, 2011.

Extended European Search Report for EP Appl. No. 08778255.3 dated Aug. 3, 2010.

U.S. Appl. No. 12/523,370: Notice of Allowance and Fee(s) Due, Fee(s) Transmittal, Determination of Patent Term Adjustment, Notice of Allowababiliy dated Feb. 7, 2012; Amendment After *Ex Parte Quayle* Office Action filed Jan. 26, 2012; Preliminary Amendment in Support of Request to Participate in Patent Prosecution Highway (PPH) Program filed Aug. 15, 2011.

* cited by examiner

PRIOR ART

DEVICE AND METHOD FOR INTRODUCING GAS FOR ANALYSIS DEVICE

CROSS-REFERENCE TO RELATED APPLICATIONS

This application is a national phase application of International Application No. PCT/JP2008/062874, filed Jul. 10, 2008, and claims the priority of Japanese Application No. 2007-183292, filed Jul. 12, 2007, the contents of both of which are incorporated herein by reference.

TECHNICAL FIELD

The present invention relates to a device and a method for supplying a gas with a pressure thereof adjusted by a pressure adjusting mechanism to an analysis device such as a TEM (Transmission Electron Microscope), an SEM (Scanning Electron Microscope), an XPS (X-ray Photoelectron Microscope), an AES (Auger Electron Spectroscopy), or an EPMA (Electron Probe Micro Analysis).

BACKGROUND ART

As a conventional technique of the present invention, Patent Document 1 describes "an X-ray diffraction device and a position sensitive gas-filled X-ray counter" used for the device, for example.

FIG. 2 schematically illustrates the above-stated conventional X-ray diffraction device. Reference numeral 4 denotes a measurement chamber of a high vacuum atmosphere, inside of which a position sensitive gas-filled X-ray counter 5 is provided. Reference numeral 2 denotes a specimen. Incident X-ray 1 is incident to the specimen 2 in the direction of the arrow. The direction of diffracted X-ray 3 will be varied depending on the specimen, and when the specimen is a polycrystal, for example, the light will be diffracted in a plurality of directions concurrently as illustrated in FIG. 2. The plurality of diffracted X-rays 3 are counted concurrently by the position sensitive X-ray counter 5.

The position sensitive X-ray counter 5 includes double-layered X-ray transmission windows 6 and 7 opposed to each other with a predetermined gap (e.g., 10 mm) therebetween, each having an arc shape (e.g., extending at the angle of 120°) centered about a measurement position of the specimen, where an inside of the inner X-ray transmission window 7 (a first window) is called a counter unit 11, and an inside of the outer X-ray transmission window 6 (a second window) is called a vacuum vessel unit 10. The X-ray transmission window 6 is made of a high-polymer organic film of 2.5 µm in thickness, and the X-ray transmission window 7 is made of a beryllium film of 7.5 µm in thickness. An operation gas is filled in the counter unit 11, and electrodes 8 and 9 are disposed therein.

Reference numeral 22 denotes a plurality of gas cylinders, from which a plurality of gases are introduced to a gas mixer 21 via pressure reducing valves to set the composition of gas. Reference numeral 18 denotes a pressure regulator including a pressure indicator, a variable leak valve, and a controller not illustrated. In accordance with a difference between a preset pressure and a measurement pressure by the pressure indicator not illustrated, the controller performs PID (proportional-plus-integral-plus-derivative) control to open/close a variable leak valve 19 so as to adjust conductance, thus supplying the operation gas to the counter unit 11 while keeping a gas pressure constant. Reference numeral 20 denotes a rotary pump. The pressure can be controlled by adjusting the variable leak valve 19 and a gain and a time constant of the controller in the pressure regulator 18. That is, the operation gas composition and the pressure control (adjusting) mechanism are used so as to regulate the counter efficiency of the X-ray counter and the X-ray transmittance to be optimal values in accordance with the energy of the X-ray measured.

The vacuum vessel unit 10 is evacuated by a turbo molecular pump 14 and a rotary pump 15. Reference numeral 16 denotes a vacuum gage, based on which if the pressure of the vacuum vessel unit 10 is higher than a preset threshold because of breakage of the X-ray transmission window 7, a closing valve 17 is closed automatically, thus preventing leakage of the operation gas to the measurement chamber 4 of a high vacuum atmosphere.

When air is to be leaked to the counter unit 11, the vacuum vessel unit 10, or the measurement chamber 4 of a high vacuum atmosphere, the leaking has to be conducted while keeping the pressures of the counter unit 11, the vacuum vessel unit 10, and the measurement chamber 4 equal so as to prevent the breakage of the X-ray transmission windows 6 and 7. To this end, the valve 17 is firstly closed to shut off the supply of the operation gas and reduce the pressure of the counter unit, followed by opening of the valves 23, 24, and 25 to make the pressures of the units 11, 10, and 4 equal, and then the leak valve 26 is opened so as to introduce dry air passing through an air drier 27. In this operation, in order to minimize a differential pressure applied to the X-ray transmission windows 6 and 7, attention has to be paid so as to make conductance from the leak valve 26 to both surfaces of the X-ray transmission windows 6 and 7 equal.

Patent Document 1: JP Published Patent Application No. 05-332958 A (1993)

DISCLOSURE OF THE INVENTION

In the above-stated conventional technique, the specimen (analyte) is disposed in a high vacuum atmosphere. On the other hand, since an actual material is used in an environment different from such an atmosphere, a disparity will occur between the analysis result under high vacuum and the state of the actual material. Thus, it is desired to introduce gas to the analysis device at a position where the specimen is disposed. However, since the inside of the gas for an analysis device is under high vacuum ($10^{-2}$ Pa or less), the gas pressure has to be controlled thereto from a positive pressure ($10^5$ Pa or more) that differs by seven digits, and therefore it is not easy to achieve a target pressure and to keep the achieved pressure constant, it takes time to change the type of gas completely, and it is not easy to replicate the same condition. Thus, the difficulty arises in conducting analysis under the same conditions by a stable pressure operation and in performing reanalysis by replicating the same conditions.

It is an object of the present invention to provide a novel device and method for synthesizing a plurality of gases at cylinder pressures and supplying the synthesized gas into an analysis device under high vacuum, whereby the above problems can be solved.

In order to cope with the above-stated problems, the device for introducing a gas for an analysis device of the present invention includes: a gas synthesis unit that synthesizes a plurality of types of gases in a mixing chamber; a pressure adjusting unit that introduces the gas synthesized in the gas synthesis unit for pressure reduction; a gas switching unit including a gas switching valve that performs switching so as to introduce the depressurized gas from the pressure adjusting unit to a gas analysis device, and a gas analysis device that analyses a component of the synthesized gas. The gas synthesis unit includes a plurality of gas introducing paths leading from a plurality of gas sources to the mixing chamber via a pressure valve, a path for exhaustion from the mixing chamber to exterior via an open/close valve, and a path for introduction from the mixing chamber to the pressure adjusting unit via a flow-adjusting valve. The pressure adjusting unit includes an introducing chamber that introduces gas from the gas synthesis unit, a path provided with a pump that reduces the pressure of the gas introduced in the introducing chamber to a pressure ranging from 0.1 Pa to 0.1 MPa, and a path leading from the introducing chamber to the gas switching unit. The gas switching unit includes a path guiding the gas from the pressure adjusting unit to the analysis device via the gas switching valve, and a path for exhaustion to exterior via a pump.

In addition to the above-stated features, the device for introducing a gas for an analysis device of the present invention includes a gas controlling unit. The gas controlling unit controls the pressure valve of the gas synthesis unit so as to adjust the gas synthesized in the gas synthesis unit, controls the pump of the pressure adjusting unit so as to allow the pressure adjusting unit to reduce the pressure of the introduced gas to a desired pressure, and switches the gas switching valve to supply a desired type of gas to the analysis device.

Further, in addition to the above-stated features, in the device for introducing a gas for an analysis device of the present invention, the gas control unit opens the pressure valve of the gas synthesis unit, drives the pump of the gas switching unit, and discharges a gas in the path from the mixing chamber to the switching valve in order to change a gas to be supplied to the analysis device.

Furthermore, in addition to the above-stated features, in the device for introducing a gas for an analysis device of the present invention, the gas switching valve introduces a desired gas in a desired path selected from among a plurality of paths to the analysis device.

The method for introducing a gas for an analysis device of the present invention comprises the steps of: mixing a plurality of types of gasses in a mixing chamber of a gas synthesis unit; adjusting the flow rate of the mixed gas so as to introduce the mixed gas to a pressure adjusting unit; reducing the pressure of the introduced gas in the pressure adjusting unit with a pump to a preset pressure ranging from 0.1 Pa to 0.1 MPa; and introducing the gas depressurized to the above pressure to the analysis device via the gas switching valve of the gas switching unit.

In addition to the above-stated features, the method for introducing a gas for an analysis device of the present invention comprises: controlling a pressure valve provided to the gas synthesis unit so as to adjust a gas to be synthesized in the gas synthesis unit; controlling the pump of the pressure adjusting unit so as to reduce the pressure of the introduced gas to the preset pressure in the pressure adjusting unit; and controlling the supply of a desired type of gas to the analysis device by switching the gas switching valve.

In addition to the above-stated features, the method for introducing a gas for an analysis device of the present invention comprises opening an open/close valve of the gas synthesis unit and driving a pump of the gas switching unit so as to discharge the gas in the path from the mixing chamber to the switching valve in order to change a gas to be supplied to the analysis device.

In addition to the above-stated features, according to the method for introducing a gas for an analysis device of the present invention, the gas switching valve guides a desired gas in a desired path selected from among a plurality of paths to the analysis device.

The present invention is configured as described above such that when a change in a substance under a gas atmosphere is analyzed for an analysis device of a high vacuum atmosphere, a desired gas can be supplied precisely and stably, whereby the analysis is enabled while keeping the same conditions and replicating the conditions.

In addition, according to the present invention, a gas supplied to an analysis device can be switched to a different desired gas in a short period of time by simple operations, which is the effect of the present invention.

According to the present invention, in order to respond to needs of analyzing a change in material structure at a nano-level because higher-functionally materials are developed, atmosphere required can be controlled precisely to satisfy the needs, thus contributing to precise analysis of material behavior.

BEST MODE FOR CARRYING OUT THE INVENTION

The following describes an embodiment of the present invention with reference to the drawings.

Figure 1:
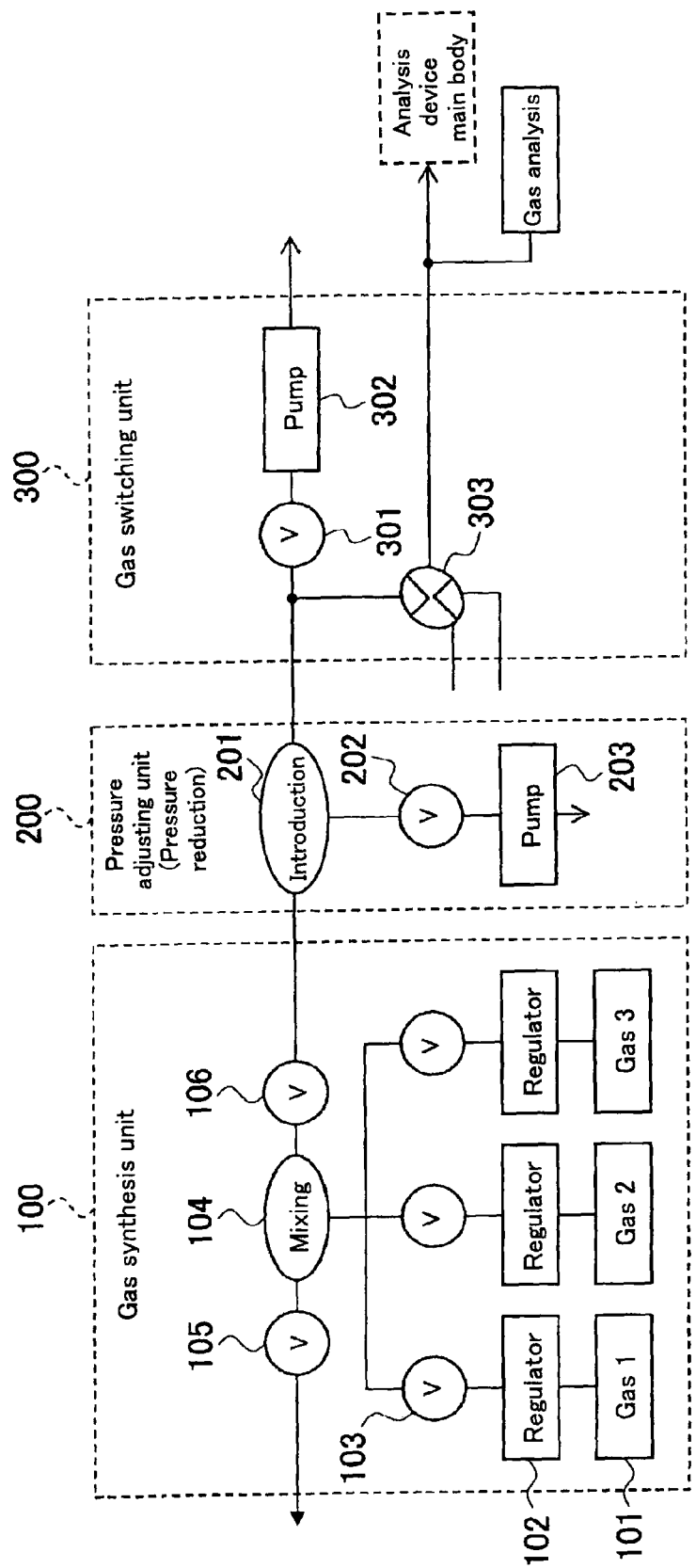
FIG. 1 illustrates the overall configuration of a device for introducing a gas for an analysis device according to the present invention.
Figure 2:
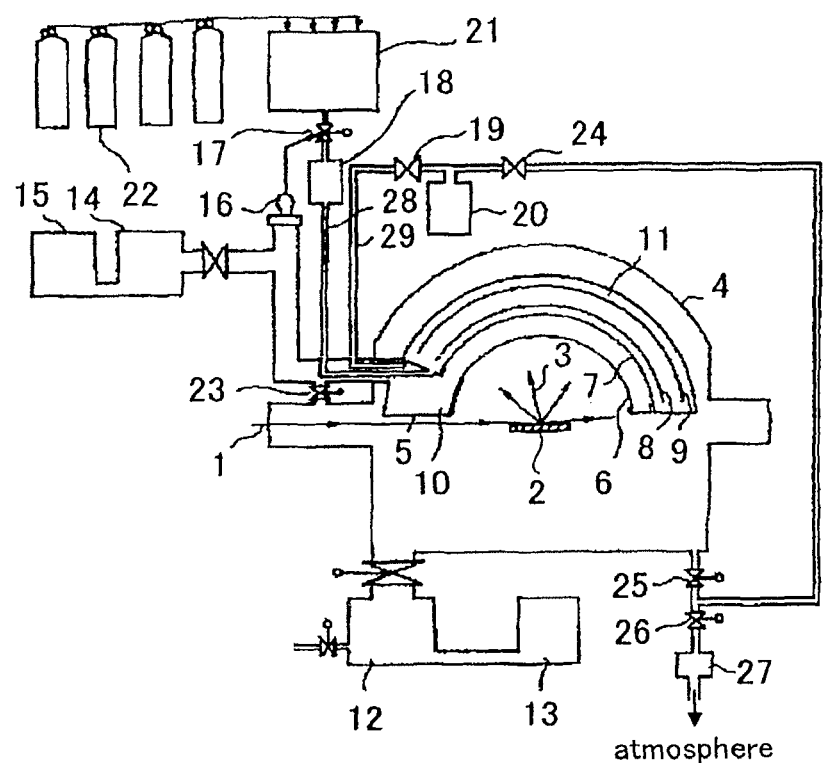
FIG. 2 schematically illustrates a conventional X-ray diffraction device.

FIG. 1 illustrates the overall configuration of a device for introducing a gas for an analysis device according to the present invention. As illustrated in FIG. 1, the device for introducing a gas of the present invention includes a gas synthesis unit 100, a pressure adjusting unit 200, and a gas switching unit 300.

The gas synthesis unit 100 includes a gas supply source 101 such as a gas cylinder, a regulator 102, a valve 103, a mixing chamber 104, and valves 105 and 106. Pressure of a gas supply source 101 such as a gas cylinder each filled with a different type of gas is a high pressure of about 16 MPa, from which gas is introduced to the mixing chamber 104 through the regulator 102 and the valve 103 so as to synthesize gas of a desired gas component. Pressure of the gas in the mixing chamber 104 is about 0.2 to 0.4 MPa that is close to an atmospheric pressure.

The gas synthesized in the mixing chamber is introduced to an introducing chamber 201 in the pressure adjusting unit 200 via the flow-adjusting valve 106. The flow rate in this case is 100 cc/min or less. The introducing chamber is connected with a pressure reducing pump 203 via a valve 202, by which the pressure of the gas in the introducing chamber 201 is reduced to about 0.1 Pa to 0.1 MPa. If necessary, the pressure adjusting unit 200 may be configured with a plurality of stages. In such a case, the pressure of the introduced gas may be reduced finally to about 0.1 Pa to 0.1 MPa in the pressure adjusting unit 200.

In the above-stated device, when the component of the gas to be synthesized in the gas synthesis unit is changed, inert gas is introduced from a gas supply source 101 filled with the inert gas to the mixing chamber, followed by opening of the valve 105, the valves 106 and 301 are further opened, and a pump 302 in the gas switching unit 300 is driven. In this way, old gas in a gas supply line from the mixing chamber to a switching valve 303 is exhausted using the inert gas. Then, the valve 105 is closed, and new gas is introduced to the mixing chamber for synthesis.

In this way, the old gas in the mixing chamber is replaced with the inert gas within a few seconds and the new gas is synthesized within a few minutes, thus starting the supply of the new gas to an analysis device.

As the above-stated gas line, a plurality of lines may be provided, such as an oxidizing line, a reducing line, and an inert line in accordance with types of gases to be synthesized, and a desired gas may be supplied to the analysis device by the operation of the switching valve 303 provided in the gas switching unit.

INDUSTRIAL APPLICABILITY

The present invention is applicable to a device and a method for supplying a gas with a pressure thereof adjusted by a pressure adjusting mechanism to an analysis device such as a TEM, an SEM, an XPS, an AES, or an EPMA.

The invention claimed is:

1. A device for introducing a gas for an analysis device, which includes: a gas synthesis unit that synthesizes a plurality of types of gases in a mixing chamber; a pressure adjusting unit that introduces the gas synthesized in the gas synthesis unit for pressure reduction; a gas switching unit including a gas switching valve that performs switching so as to introduce the depressurized gas from the pressure adjusting unit to an analysis device main body, and a gas analysis device that analyses a component of the synthesized gas, wherein the gas synthesis unit includes a plurality of gas introducing paths leading from a plurality of gas sources to the mixing chamber via a pressure valve, a path for exhaustion from the mixing chamber to exterior via an open/close valve, and a path for introduction from the mixing chamber to the pressure adjusting unit via a flow-adjusting valve, wherein the pressure adjusting unit includes an introducing chamber that introduces gas from the gas synthesis unit, a path provided with a pump that reduces the pressure of the gas introduced in the introducing chamber to a pressure ranging from 0.1 Pa to 0.1 MPa, and a path leading from the introducing chamber to the gas switching unit, wherein the gas switching unit includes a path guiding the gas from the pressure adjusting unit to the analysis device via the gas switching valve, and wherein the gas switching unit includes a path guiding the depressurized gas from the pressure adjusting unit to the analysis device via the gas switching valve, and the gas switching valve performs switching so as to introduce the depressurized gas to the inside of the analysis device main body maintained at $10^{-2}$ Pa or less.

2. The device for introducing a gas according to claim 1, wherein the device is provided with a gas controlling unit, which controls the pressure valve of the gas synthesis unit so as to adjust the gas synthesized in the gas synthesis unit, controls the pump of the pressure adjusting unit so as to allow the pressure adjusting unit to reduce the pressure of the introduced gas to a desired pressure, and switches the gas switching valve to supply a desired type of gas to the analysis device main body.

3. The device for introducing a gas according to claim 2, wherein the gas control unit opens the pressure valve of the gas synthesis unit, drives the pump of the gas switching unit, and discharges a gas in the path from the mixing chamber to the switching valve in order to change a gas to be supplied to the analysis device main body.

4. The device for introducing a gas according to claim 2, wherein the gas switching valve of the gas switching unit introduces a desired gas in a desired path selected from among a plurality of paths to the analysis device main body.

5. A method for introducing a gas for an analysis device, comprising the steps of: mixing a plurality of types of gasses in a mixing chamber of a gas synthesis unit; adjusting a flow rate of the mixed gas so as to introduce the mixed gas to a pressure adjusting unit; reducing a pressure of the introduced gas in the pressure adjusting unit with a pump to a preset pressure ranging from 0.1 Pa to 0.1 MPa; and introducing the gas depressurized to the above pressure to the inside of the analysis device main body maintained at $10^{-2}$ Pa or less via a gas switching valve of a gas switching unit, wherein the method controls a pressure valve provided to the gas synthesis unit so as to adjust a gas to be synthesized in the gas synthesis unit;

controls the pump of the pressure adjusting unit so as to reduce the pressure of the introduced gas to the preset pressure in the pressure adjusting unit;

controls the supply of a desired type of gas to the analysis device by switching the gas switching valve; and opens an open/close valve of the gas synthesis unit and drives a pump of the gas switching unit so as to discharge the gas in the path from the mixing chamber to the switching valve in order to change a gas to be supplied to the analysis device.

6. The method for introducing a gas for the analysis device according to claim 5, wherein the gas switching valve of the gas switching unit guides a desired gas in a desired path selected from a plurality of paths to the analysis device main body.

* * * * *